United States Patent [19]

Harris et al.

[11] 4,287,370

[45] Sep. 1, 1981

[54] HYDROFORMYLATION PROCESS FOR THE PRODUCTION OF N-VALERALDEHYDE

[75] Inventors: Norman Harris, Stockton-on-Tees; Alan J. Dennis, Acklam; Thomas F. Shevels, Stockton-on-Tees, all of England

[73] Assignee: Davy McKee (Oil & Chemicals) Limited, London, England

[21] Appl. No.: 132,292

[22] Filed: Mar. 20, 1980

[30] Foreign Application Priority Data

Mar. 21, 1979 [GB] United Kingdom ............... 10012/79
Nov. 28, 1979 [EP] European Pat. Off. ........ 79302709.5

[51] Int. Cl.³ .......................................... C07C 45/50
[52] U.S. Cl. .................................................. 568/454
[58] Field of Search ....................................... 568/454

[56] References Cited

U.S. PATENT DOCUMENTS

| | | | |
|---|---|---|---|
| 3,290,379 | 12/1966 | Eisenmann | 568/454 |
| 3,527,809 | 9/1970 | Pruett | 568/454 |
| 3,954,877 | 5/1976 | Gipson | 568/454 |
| 3,965,192 | 6/1976 | Booth | 568/454 |
| 4,148,830 | 4/1979 | Pruett | 568/454 |

FOREIGN PATENT DOCUMENTS

| | | | |
|---|---|---|---|
| 853377 | 4/1977 | Belgium | 568/454 |
| 2715685 | 10/1977 | Fed. Rep. of Germany | 568/454 |
| 1338237 | 11/1973 | United Kingdom | 568/454 |

OTHER PUBLICATIONS

Knap et al. "Chem., Engr. Progr." vol. 62, No. 4, p. 74 (1966).
Wakamatsu "Nippon Kagaku Zasshi" vol. 85, (3) pp. 227-231 (1964).
Wakamatsu "Chem. Abstr." vol. 61, p. 13173 (1964).

Primary Examiner—Werren B. Lone
Attorney, Agent, or Firm—Bernard, Rothwell & Brown

[57] ABSTRACT n-Valeraldehyde is produced by hydroformylation of butene-1 in the presence of one or more of cis- and trans-butene-2 and iso-butylene using a rhodium complex catalyst such as $HRh(CO)(PPh_3)_3$. Reaction conditions include use of at least about 100 moles of free triorganophosphine per gram atom of rhodium, a temperature of about 80° C. to about 130° C., a total pressure of not more than about 50 kg/cm² absolute, a partial pressure of carbon monoxide of not more than about 1.5 kg/cm² absolute, and a partial pressure of hydrogen of from about 1.0 to about 7.5 kg/cm² absolute. An n-/iso-ratio of 20:1 and a conversion efficiency of butene-1 to n-valeraldehyde of over 85% are possible under these conditions with essentially no resin formation despite the presence of iso-butylene. The n-/iso-valeraldehyde mixture can be aldolized and reduced without intermediate purification to give a commercially acceptable $C_{10}$-plasticizer alcohol.

14 Claims, 1 Drawing Figure

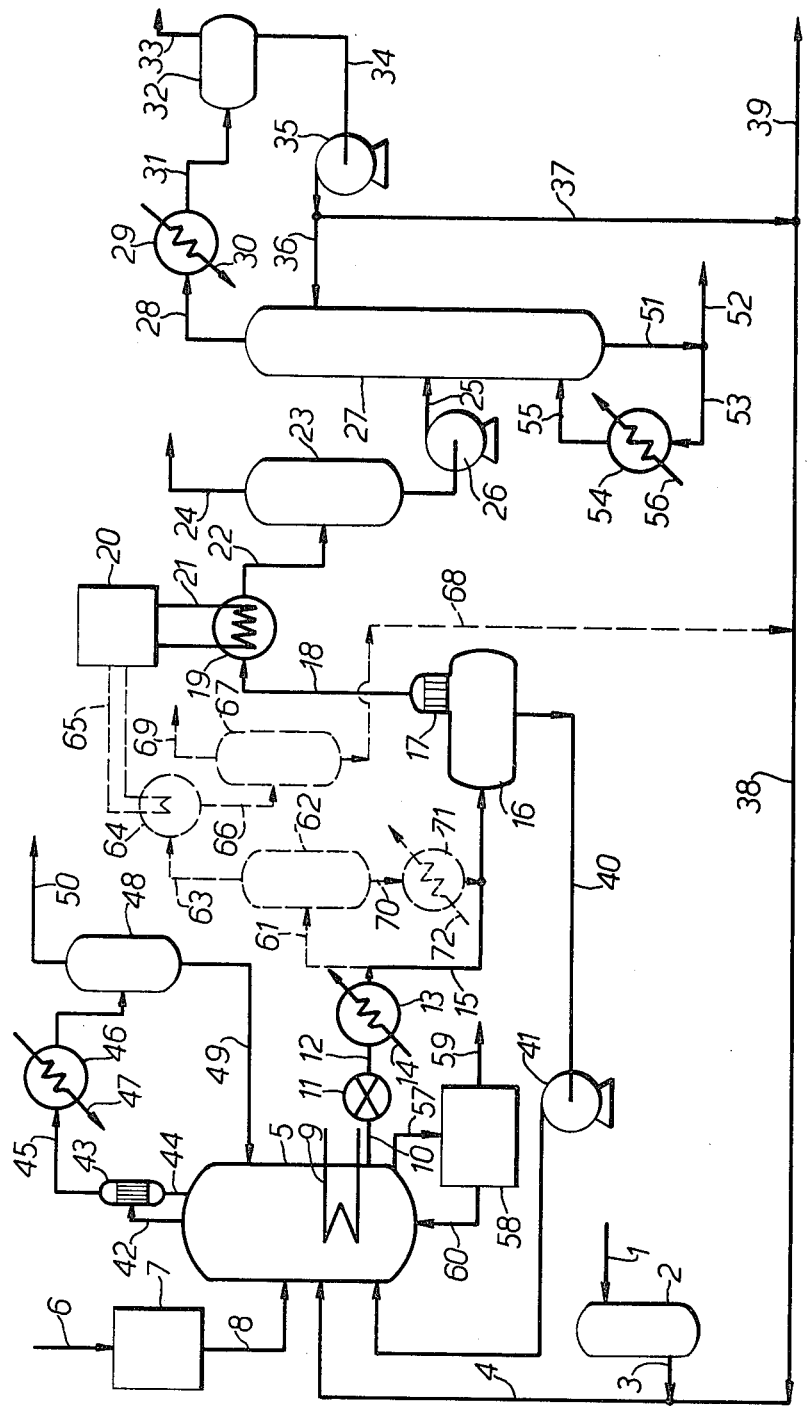

HYDROFORMYLATION PROCESS FOR THE PRODUCTION OF N-VALERALDEHYDE

This invention relates to a process, more particularly to a hydroformylation process for the production of n-valeraldehyde from butene-1 in a mixed $C_4$-olefin feedstock.

The reaction of an olefin with hydrogen and carbon monoxide in the presence of a suitable catalyst to form an aldehyde having one more carbon atom than the starting olefin is well known in the art. Such a reaction is termed variously an "oxo" reaction, oxonation or hydroformylation. A variant of such a reaction using modified catalysts to yield alcohols rather than aldehydes as the major product is also known.

Although the simplest olefin, ethylene, gives rise to a single aldehyde, i.e. propionaldehyde, upon hydroformylation, propylene may yield two aldehydes, i.e. n- and iso-butyraldehyde, depending on which of the two carbon atoms of the olefin bond becomes bonded to the carbon atom of the carbon monoxide reactant. The proportions of n- and iso-butyraldehydes formed depend on the reaction conditions used and the nature of the catalyst. Generally speaking the n-aldehyde is usually more desirable commercially than the corresponding iso-product which is often burnt as a fuel since there is insufficient demand for it. More than two aldehydes may arise with higher terminal olefins, such as hexene-1 or octene-1, since there is the potential for izomerization of the molecule with migration of the olefinic double bond. In all hydroformylation reactions another by-product is the alkane corresponding to the starting olefin. This is formed under the reaction conditions by hydrogenation.

The initial work on hydroformylation used cobalt-containing catalysts such as cobalt octacarbonyl. However the use of such catalysts is generally disadvantageous since it is necessary to work at extremely high pressures of up to several hundred atmospheres, since product recovery is difficult and since it is difficult to obtain n-/iso-product aldehyde ratios of higher than about 4:1.

More recently a rhodium catalysed hydroformylation process has been developed for hydroformylation of terminal olefins. This has also been put into practice commercially. This process has the advantage of requiring a low pressure of about 20 kg/cm$^2$ absolute or less, of allowing a simple product recovery step and of yielding high n-/iso-product aldehyde ratios of 10:1 and higher. This process is described, for example, in U.S. Pat. No. 3,527,809 and in British Pat. No. 1338237 and involves the use of an organo-phosphorus ligand in addition to a rhodium complex compound. A further description of the process will be found in an article entitled "Low-pressure OXO process yields a better product mix", Chemical Engineering, Dec. 5, 1977 and in West German Offenlegungsschrift No. 2715685.

In the process described in U.S. Pat. No. 3,527,809 the hydroformylation reaction with the terminal olefin is conducted under a defined set of variables which include (1) the rhodium complex catalyst, (2) the olefinic feed, (3) the triorganophosphorus ligand and its concentration, (4) the relatively low temperature range, (5) the relatively low total gas pressure, and (6) the partial pressure exerted by hydrogen and carbon monoxide. A typical active catalyst species is hydridocarbonyltris (triphenylphosphine) rhodium (I) which has the formula $HRh(CO)(PPh_3)_3$. Excess triphenylphosphine is used with this catalytic species. Among the olefins mentioned in this specification is butene-1 (see column 4 line 40). However no details are given of any experiments on butene-1 using the rhodium catalyst and, although Example 77 refers to the use of but-1-ene in Example 9, this appears to be a misprint since Example 9 uses oct-1-ene. Moreover there is no suggestion to use the process with mixed olefins.

A development of this process is described in British Pat. No. 1338237. This involves the use as a diluent of high boiling liquid condensation products of the product aldehydes, e.g. a mixture of trimers (III) and (IV) and tetramer (VII) whose formulae are given on page 4 of the printed specification. Amongst the olefins that are listed for use in this process is 1-butene (see page 7 line 68 of the printed specification). However, no experimental work describing the use of 1-butene is given in British Pat. No. 1338237. There is no suggestion to operate the process with a mixed olefin feed.

In West German Offenlegungsschrift No. 2715685 it is proposed to hydroformylate $C_2$ to $C_5$ $\alpha$-olefins by a rhodium-catalysed process in which the volume of catalyst-containing liquid in the reactor is controlled by recycling gas through the reactor at a rate such that product aldehyde and higher boiling aldehyde condensation products are removed at the same rate at which they are formed. Butene-1 is mentioned as a suitable olefin. However, no experimental details are given of any work utilising butene-1, the olefin specifically exemplified in the drawing and in the sole Example being propylene. There is no suggestion to operate using a mixed olefin feed.

Ethylene and propylene are commercially available as substantially pure feedstocks. Although large quantities of butylenes are produced in petroleum refineries, separation of pure butene-1 from a mixed $C_4$ hydrocarbon stream adds appreciably to cost. Such mixed $C_4$-olefin feed streams typically contain, in addition to butene-1, cis- and trans-butene-2 and isobutylene as well as minor amounts of n- and iso-butane and traces of propane and pentane. Hence it is economically attractive to utilise such a feed stream as a source of butene-1 without purification of butene-1.

A hydroformylation process is operated commercially in the United States of America using a mixed $C_4$-olefin feed stream and a cobalt catalyst. This results in production of a mixture of n- and iso-valeraldehydes, both butene-1 and butene-2 (cis- and transforms) being converted to $C_5$ aldehyde products. However the n-/iso-aldehyde product ratio is only about 3:1 to 4:1. The process suffers all the disadvantages attendant upon the use of a cobalt catalyst, such as difficult product recovery and use of high reaction pressures. An additional problem is that iso-butylene reacts with the product aldehyde under the hydroformylation reaction conditions to form resins which complicate the already difficult work up process associated with the use of cobalt as a catalyst. To avoid such resin formation it is necessary to remove iso-butylene from the $C_4$-olefin feedstock by, for example, an acid washing step. This adds to the operating costs and energy requirements of the process.

Although the published literature on the commercial low pressure rhodium-catalysed hydroformylation reaction concentrates on hydroformylation of terminal olefins, and commercial operation thereof is as yet confined to hydroformylation of ethylene and propylene, there are reports in the literature of internal olefins being successfully hydroformylated using rhodium catalysts. Thus, it has been reported that, with rhodium catalysts, internal olefins react faster than terminal ones (see H. Wakamatsu: Nippon Kagaku Zasshi 85, (3), 227–231 (1964): Chem. Abs., 61, 13173(1964)).

Experimental work on hydroformylation of butenes with rhodium catalysts has appeared in Japanese Patent Publication No. 575/66 (Japanese Patent Application No. 12124/63). This reports that, using rhodium carbonyl as catalyst, butene-2 can be hydroformylated at a temperature of not more than 80° C. to give iso-valeraldehyde ($\alpha$-methylbutyraldehyde). The production of optically active 2-methylbutyraldehyde (iso-valeraldehyde) by hydroformylation of butene-1 and also of butene-2 using chloro-dicarbonyl rhodium dimer [$Rh(CO)_2Cl$]$_2$ and an optically active diphosphine as co-catalyst has been described in Japanese Unexamined Patent Publication 52/057108. Hydroformylation of butene-1 using $RhH(CO)(PPh_3)_3$ as catalyst and $P(OPh)_3$ as co-catalyst is reported in Japanese Examined Patent Publications 73/40326 and 73/43799.

Hydroformylation of butene-1 in the presence of a rhodium catalyst to give a mixture of n- and iso-valeraldehydes has been described (see German Patentschrift No. 953605). The hydroformylation of iso-butylene has been reported (see J. E. Knap, N. R. Cox and W. R. Privette, Chem, Eng. Progr. 62, No. 4, 74 (1966)).

A proposal has also been made to produce a mixture of $C_3$ to $C_5$ aldehydes by hydroformylation, using a rhodium catalyst such as hydridocarbonyltris (triphenylphosphine) rhodium (I), of a gas formed in the autothermal cracking of petrol, which contains 5 to 30% ethylene, 1 to 10% propylene and up to 5% butylene. This proposal is described in French Patent Specification No. 2249061. The experimental details given do not disclose whether any butene-1 is present in the ethylene-containing feed gas.

From these reports of the published work it would appear that use of a mixed $C_4$-olefin feed in a rhodium catalysed hydroformylation process would result in a mixture of n-valeraldehyde, iso-valeraldehyde (2-methylbutyraldehyde) and 2,2-dimethylpropionaldehyde by reaction respectively of butene-1, butene-2 and iso-butylene. Hence it would be expected that, in order to achieve a high n-/iso-product aldehyde ratio, it would be necessary to utilise essentially pure butene-1 as a feedstock.

The present invention seeks to provide a rhodium-catalysed hydroformylation process for the production of n-valeraldehyde from a mixed $C_4$-olefin feedstream under conditions minimising formation of iso-valeraldehyde and 2,2-dimethylpropionaldehyde as well as minimising formation of resins by reaction of iso-butylene with product aldehyde, whereby n-/iso-ratios of at least about 8:1 are attained.

We have now discovered that n-valeraldehyde can be produced by hydroformylation of butene-1 in a mixed $C_4$-olefin feedstream using a rhodium complex compound catalyst at high conversion of butene-1, with a very good n-/iso-product aldehyde ratio and with low conversion of butene-1 to butane and/or butene-2, by use of a large excess of triorganophosphorus ligand and by careful control of temperature and partial pressures of the reactants and/or products.

According to the present invention a hydroformylation process for the production of n-valeraldehyde comprises contacting a $C_4$-olefin feedstock with carbon monoxide and hydrogen in a hydroformylation zone in the presence of a catalytic quantity of a rhodium complex catalyst, said $C_4$-olefin feedstock comprising butene-1 and at least one other $C_4$-olefin selected from cis-butene-2, trans-butene-2, and iso-butylene and said rhodium complex catalyst comprising rhodium in complex combination with carbon monoxide and a triorganophosphine ligand, and in the presence of at least about 100 moles of free triorganophosphine ligand per gram atom of rhodium, at a temperature in the range of from about 80° C. to about 130° C., and at a total pressure of not more than about 50 kg/cm$^2$ absolute, the partial pressure of carbon monoxide being less than about 1.5 kg/cm$^2$ absolute and the partial pressure of hydrogen being in the range of from about 1.0 to about 7.5 kg/cm$^2$ absolute, and recovering from the hydroformylation zone unreacted $C_4$-olefins and n-valeraldehyde.

Under our chosen hydroformylation conditions cis- and trans-butene-2 are hydroformylated extremely slowly, as also is iso-butylene. Moreover our process is characterised by a marked absence of any resin formation when the $C_4$-olefin feedstock contains iso-butylene.

Under hydroformylation conditions butene-1 can undergo various reactions. Thus, besides the desired production of n-valeraldehyde, some of the butene-1 may also be converted to the corresponding iso-aldehyde, i.e. iso-valeraldehyde. These aldehydes can condense each with itself or with the other aldehyde to form a series of dimers, trimers, tetramers and other higher molecular weight products as will be described below. Additionally, we have found that isomerization of butene-1 to cis- and trans-butene-2 can occur in the presence of the hydroformylation catalyst. Such isomerization cannot occur with ethylene or propylene. Since, under our chosen hydroformylation conditions cis- and trans-butene-2 are hydroformylated extremely slowly compared with butene-1, cis- and trans-butene-2 behave essentially as an inert material in the reaction. Hence isomerization of butene-1 to butene-2 results in a corresponding reduction in overall yield of aldehyde product from butene-1. A further reaction that can occur is reduction of butene-1 to n-butane.

In a commercial plant it is a desirable objective to maximise conversion of the butene-1 present in the $C_4$-olefin feedstock to n-valeraldehyde and to minimise formation of the iso-aldehyde, conversion of butene-1 to cis- and trans-butene-2, and reduction of butene-1 to n-butane. We have found that this objective can be achieved by use of the specified partial pressure conditions and by the use of a temperature within the given range, together with the use of a large excess of the triorganophosphine ligand. In some of our experiments we have found that butene-1 was converted to n-valeraldehyde with an efficiency of over 85% and at an n-/iso-product aldehyde ratio of more than 20:1.

In the process of the invention iso-butylene does not form resins with product n-valeraldehyde to any appreciable extent. Hence it is not necessary to acid wash or otherwise pretreat the feedstock in order to remove iso-butylene therefrom, as is necessary in the corresponding cobalt-catalysed reaction.

The process is operated at temperatures in the range of from about 80° C. to about 130° C. As the temperature is increased, so the rate of isomerization of butene-1 to butene-2 increases. In some of our experiments we found that as much as 30% of the butene-1 isomerizes to form butene-2 at temperatures of 130° C. or higher, whereas at 110° C. approximately 5% by conversion to butene-2 was detected. This figure fell to about 3% at 100° C. and to between 1 and 2% at 90° C. Thus it is preferred to operate at temperatures of about 120° C. or below, more preferably at temperatures in the range of from about 90° C. to about 110° C. In contrast, ethylene and propylene can be hydroformylated successfully at temperatures of up to 145° C. to give high yields of aldehyde product and only small amounts of by-products.

In U.S. Pat. No. 3,527,809 it is recommended that there should be at least two moles of the triorganophosphorus ligand per mol (gram atom) of rhodium, and preferably at least 5 mols of free triorganophosphorus ligand per mol of rhodium. Example 76 of that specification shows a molar ratio of triphenylphosphine to rhodium of about 55:1 and the practical upper limit is said to be approximately 100:1, with an upper limit of about 30:1 being considered, for most instances, to be within the contemplated commercially attractive area (see column 5 line 63 to column 6 line 4 of U.S. Pat. No. 3,527,809). We have found that in the hydroformylation of a mixed $C_4$-olefin feedstock it is best to operate with at least about 100 moles, preferably at least about 150 moles up to about 500 moles or more of free triarylphosphine ligand per gram atom of rhodium. Approximately 1000 moles of free ligand per gram atom of rhodium can be considered as the practical upper limit of operation.

The triorganophosphine ligand can be a trialkylphosphine, such as tributylphosphine, or an alkyl-diaryl-phosphine, such as butyldiphenylphosphine, or an aryl-dialkyl-phosphine, such as phenyl-dibutylphosphine. Preferably, however, the triorganophosphine ligand is a triarylphosphine ligand, such as triphenylphosphine. However, other ligands such as tri-p-tolylphosphine, trinaphthylphosphine, phenyldinaphthylphosphine, diphenylnaphthylphosphine, tri-(p-methoxyphenyl)phosphine, tri-(p-cyanophenyl)phosphine, tri-(p-nitrophenyl)phosphine, p-N,N-dimethylaminophenyl bisphenyl phosphine, and the like can be used if desired. Mixtures of triorganophosphines can be used.

The total pressure is not more than about 50 kg/cm² absolute. This is equal to the sum of the partial pressures of the reactants and of the products and of any inert materials that may be present. Usually the total pressure will be at least about 4 kg/cm² absolute, but not more than about 20 kg/cm² absolute.

The partial pressure of carbon monoxide should be less than about 1.5 kg/cm² absolute, preferably less than about 1.0 kg/cm² absolute. Usually it will be preferred to operate at a partial pressure of carbon monoxide of at least 0.1 kg/cm², e.g. in the range of from about 0.5 to about 1.0 kg/cm² absolute. If partial pressures of carbon monoxide in excess of about 1.0 kg/cm² absolute are used it is found that the n-/iso-product aldehyde ratio tends to be adversely affected.

Another feature of importance is the partial pressure of hydrogen. This preferably lies in the range of from about 1.0 to about 5.0 kg/cm² absolute, more preferably about 1.0 to about 3.0 kg/cm² absolute. Although higher partial pressures of hydrogen than 5.0 kg/cm² absolute may be used without adverse effect on the course of the reaction, the use of such high hydrogen partial pressures means that, in a discontinuous or batch process, the excess unreacted hydrogen must be vented to the atmosphere or that, in a continuous process, an uneconomically large purge stream must be used in order to prevent build-up of by-products. In either case the loss of relatively expensive hydrogen represents an unnecessary cost. Usually it will be preferred to operate at hydrogen partial pressures of from about 1.25 to about 3.0 kg/cm² absolute.

The butene-1 partial pressure in the process of the invention is preferably less than about 4.0 kg/cm² absolute. Usually it will be preferred to operate at a butene-1 partial pressure in the range of from about 0.4 kg/cm² absolute up to about 3.0 kg/cm² absolute, preferably in the range of from about 0.4 kg/cm² absolute up to about 1.5 kg/cm² absolute. Although the use of higher butene-1 partial pressures does not affect significantly the n-/iso-product aldehyde rate or the conversion of butene-1 to aldehydes, there is no advantage in using higher butene-1 partial pressures than 4.0 kg/cm² since this requires the presence of a larger proportion of butene-1 in the liquid reaction phase and hence results in an increase in volume of liquid in the hydroformylation zone, thus requiring the use of a larger reactor. Furthermore the higher the partial pressure of butene-1 is, the higher is the concentration of butene-1 in any gas purge stream and hence the greater the loss of butene-1.

The $C_4$-olefin feedstock may be introduced into the hydroformylation zone in liquid or in gaseous form; it may contain, in addition to butene-1, one or more of cis- and trans-butene-2, iso-butylene, n- and iso-butane and traces of other hydrocarbons such as propane and pentane. The proportion of butene-1 in the $C_4$-olefin feedstock may vary within wide limits, for example from about 10 mole % up to about 90 mole % or more. Typically, however, the $C_4$-olefin feedstock comprises from about 20 mole % up to about 80 mole % of butene-1. Such a feedstock is desirably free from inhibitors such as butadiene, and catalyst poisons, such as sulphurous compounds and chlorine compounds. Hence the mixed $C_4$-olefin feedstock is preferably pretreated to lower the levels of these inhibitors, as for example by hydrofining to remove butadiene, and to remove substantially all the catalyst poisons, as for example by treatment with alumina and/or zinc oxide for the removal of gaseous sulphur compounds and by treatment with copper impregnated carbon for the removal of gaseous chlorinated impurities. In one procedure the $C_4$-olefin feedstock is desulphurized by passage over alumina and/or zinc oxide, then optionally dechlorinated by contact with copper impregnated carbon, and thereafter distilled to give a butene-1, sulphur-free overhead stream which can be passed to the hydroformylation zone and a bottom stream rich in cis- and trans-butene-2. This procedure is described more fully in co-pending patent application Serial No. 132,293 (Case A) by Harris, Flintoff and Kippax, filed simultaneously, Mar. 20, 1980, herewith, the disclosure of which is incorporated herein by reference.

The material fed to the hydroformylation reaction zone (i.e. the $C_4$-olefin feed and/or the synthesis gas) may include one or more inert gaseous materials such as nitrogen. Furthermore the presence of small quantities of oxygen, e.g. up to about 0.1% by volume, is not deleterious to the conversion of butene-1 to product n-valeraldehyde, although provision must be made in this case for removal of triorganophosphine oxide and for replenishment of the reaction zone with a corresponding amount of triorganophosphine.

The aldehyde products will exert a partial pressure at the reaction temperature employed. Thus the aldehyde partial pressure may range from about 0.2 kg/cm² absolute up to about 1.0 kg/cm² absolute or more. Typically it is about 0.5 kg/cm² absolute to about 0.8 kg/cm² absolute.

The catalyst used in the process of the invention is a rhodium complex catalyst comprising rhodium complexed with carbon monoxide and a triorganophosphine ligand. The catalyst is preferably free of halogen, such as chlorine, and contains hydrogen, carbon monoxide and triorganophosphine complexed with rhodium.

The catalyst will usually be present in solution. The solvent may comprise, in addition to excess ligand, an inert solvent such as toluene or cyclohexanone. Alternatively the solvent may comprise high boiling liquid condensation products rich in hydroxylic compounds. The method of formation of such liquid condensation products will be described hereinafter.

Under the reaction conditions used in the process the n- and iso-aldehyde products can each undergo condensation with itself or with the other to form a series of dimers, trimers and tetramers. Taking, for example, the reactions involved in the self-condensation of n-valeraldehyde these are postulated to be as shown in the following Table 1.

densation of n-valeraldehyde with iso-valeraldehyde and further condensation of the resulting aldol with either aldehyde to form corresponding trimers and tetramers. The condensation products are thus a complex mixture. For the sake of simplicity only the condensation products of n-valeraldehyde itself are discussed below, but it will be appreciated that reference to, for example, aldol (B) includes also the corresponding mixed n-/iso-aldol as well as the iso-/iso-aldol.

In the equations shown in Table 1 and above, the designations aldol (A), substituted acrolein (B), trimer (C), trimer (D), dimer (E), tetramer (F) and tetramer (G) are for convenience only. Aldol (A) is formed by an aldol condensation; trimer (C) and tetramer (G) are formed via Tischenko reactions; trimer (D) is formed via a transesterification reaction; dimer (E) and tetramer (F) are formed by a dismutation reaction. Principal condensation products are believed to be trimer (C), trimer (D), and tetramer (G), with lesser amounts of the other products being present. Such condensation products, therefore, contain substantial quantities of hydroxylic compounds as witnessed, for example, by trimers

TABLE 1

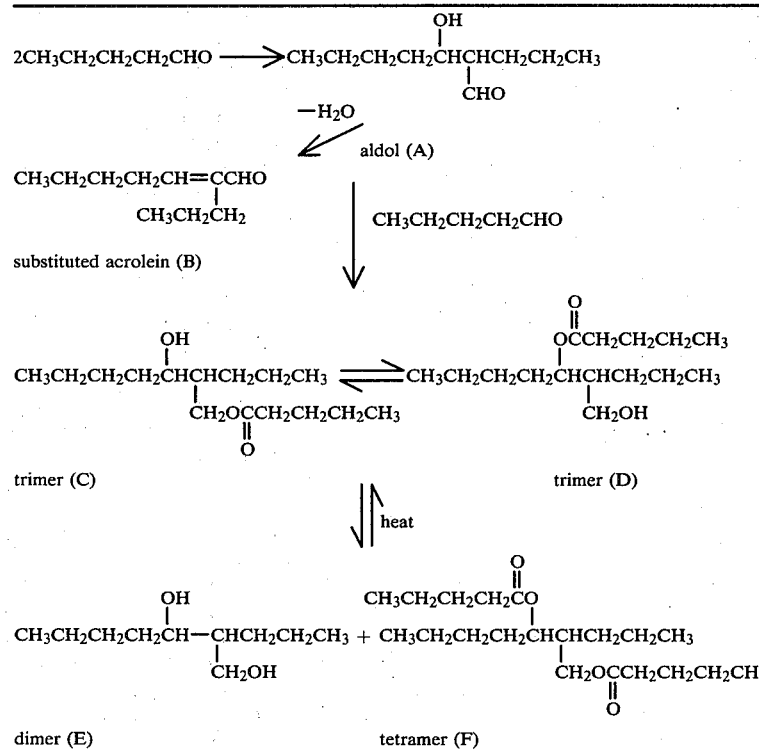

In addition aldol (A) can undergo the following reaction:

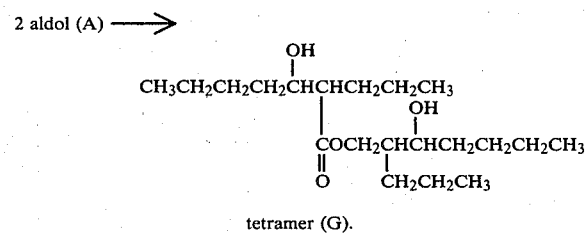

Of course the illustrated reactions involve only n-valeraldehyde. Similar products can be formed by con- (C) and (D) and tetramer (G).

From our experiments we believe that the major condensation product, which may amount to up to about 85% by weight of all high boiling aldehyde condensation products, is constituted by trimers.

The concentration of rhodium in the catalyst solution can range from about 10 parts per million by weight up to 1000 parts per million or more. However, because rhodium is a scarce and valuable metal it will usually be preferred to operate at the lowest rhodium concentration that is consistent with achieving a practicable reaction rate. Typically, the rhodium concentration lies in the range of from about 50 parts per million up to about 250 parts per million, for example in the range of from about 100 to 150 parts per million.

The rhodium may be introduced into the reaction zone in any convenient manner. For example, the rhodium salt of an organic acid can be combined with the ligand in the liquid phase and then hydrogenated, prior to introduction of the butene-1-containing feedstock and the hydrogen/carbon monoxide mixture. Alternatively the catalyst can be prepared from a carbon monoxide complex of rhodium, such as dirhodium octacarbonyl, by heating with the ligand which thereby replaces one or more of the carbon monoxide molecules. It is also possible to start with the ligand of choice and rhodium metal, or with an oxide of rhodium (e.g. $Rh_2O_3$) and the ligand, and to prepare the active species in situ during the course of the hydroformylation reaction. Yet again it is possible to introduce into the reaction zone, as a catalyst precursor, a rhodium complex such as (pentane-2,4-dionato) dicarbonyl rhodium (I) which is then converted, under the hydroformylation conditions and in the presence of excess ligand, to the operative species, e.g. rhodium hydridocarbonyl tris(triphenylphosphine). Other suitable catalyst precursors include rhodium carbonyl triphenylphosphine acetylacetonate, $Rh_4(CO)_{12}$ and $Rh_6(CO)_{16}$.

When using polymeric aldehyde condensation products as solvent, the ratio of aldehyde to such products in the liquid reaction mixture in the hydroformylation zone may vary within wide limits. Typically this ratio lies in the range of from about 1:4 to about 4:1 by weight, e.g. about 1:1 by weight.

The process can be effected discontinuously or batchwise, as for example in a pressurised batch reactor. However, it will usually be preferred to operate the process continuously.

The process can be operated using the gas recycle process described in German Offenlegungsschrift No. 2715685. Alternatively it can be operated according to the teachings of co-pending patent application Ser. No. (Case B) 132,291 by Harris and Shevels filed simultaneously herewith, the teaching of which is herein incorporated by reference.

According to an alternative procedure there is provided a process for the production of n-valeraldehyde which comprises:

(i) providing a hydroformylation zone containing a liquid charge comprising (a) a rhodium complex catalyst wherein rhodium is in complex combination with carbon monoxide and a triorganophosphine, (b) excess free triorganophosphine in an amount of at least 100 moles per gram atom of rhodium, (c) liquid n-valeraldehyde product, and (d) polymeric aldehyde condensation products;

(ii) feeding a liquid $C_4$-olefin feedstock to the hydroformylation zone, said $C_4$-olefin feedstock comprising butene-1 and at least one other $C_4$-olefin selected from cis-butene-2, trans-butene-2, and iso-butylene;

(iii) supplying make up hydrogen and carbon monoxide to the hydroformylation zone;

(iv) maintaining in the hydroformylation zone a temperature in the range of from about 80° C. to about 130° C., a total pressure of not more than about 50 kg/cm² absolute, a partial pressure of butene-1 of less than about 4.0 kg/cm² absolute, a partial pressure of carbon monoxide of less than about 1.5 kg/cm² absolute and a partial pressure of hydrogen of from about 1.0 to about 7.5 kg/cm² absolute;

(v) recovering from the hydroformylation zone a liquid reaction product;

(vi) reducing the pressure of the liquid reaction product;

(vii) thereafter flashing unreacted $C_4$-olefins and product n-valeraldehyde from the liquid reaction product;

(viii) recycling resulting liquid reaction residue, now depleted in the $C_4$-olefins and product n-valeraldehyde, to the hydroformylation zone;

(ix) condensing product n-valeraldehyde and unreacted $C_4$-olefins; and (x) recycling unreacted $C_4$-olefins to the hydroformylation zone.

In this alternative preferred process step (vii) can be effected in one or two stages. In the former case flashing produces a vaporous fraction comprising unreacted $C_4$-olefins and product n-valeraldehyde; after condensation of the mixture resulting condensate can be distilled in a distillation zone, from which a bottom product comprising n-valeraldehyde can be recovered, whilst an overhead fraction comprising unreacted $C_4$-olefins is condensed in readiness for recycling to the hydroformylation zone. In the latter case flashing in a first stage produces a first gaseous fraction comprising unreacted $C_4$-olefins which is thereafter condensed in readiness for recycling to the hydroformylation zone, whilst second stage flashing produces a second vaporous fraction containing product n-valeraldehyde which is thereafter condensed and distilled in a distillation zone to give a liquid bottom product containing n-valeraldehyde and an overhead fraction comprising $C_4$-olefins which can be condensed in readiness for recycling also to the hydroformylation zone.

Preferably in such a process part of the $C_4$-olefin condensate is purged from the system. In this way build up of unreactive cis- and trans-butene-2 and of iso-butylene is avoided. Preferably also, a gaseous purge stream is taken overhead from the hydroformylation zone in order to prevent build up therein of inert gases, such as nitrogen. A gaseous purge stream may also be taken from the n-valeraldehyde distillation zone and/or from the $C_4$-olefins condensation zone.

By effecting pressure reduction at or below reaction temperature in step (vi) followed by controlled flashing in step (vii) it can be ensured that the catalyst is not heated above reaction temperature in the performance of the process. In this way the risk of catalyst de-activation and the risk of isomerization of butene-1 to cis- or trans-butene 2 are minimised.

It is also preferred to purge at least part of the unreacted $C_4$-olefins in order to prevent build up of cis- and trans-butene-2 and of iso-butylene in the system. Such a purge stream contains considerably less butene-1 than the $C_4$-olefin feedstock, since this has largely been converted to n-valeraldehyde, and is enriched in cis- and trans-butene-2 and iso-butylene. This purge stream is of value as a feedstock for the production of butylate petroleum, for example, or can be distilled to give a butene-2 stream and an iso-butylene stream.

We have found that, by appropriate choice of reaction conditions, it is possible to achieve n-/iso- product aldehyde ratios of 20:1 or greater. Under such circumstances it is not necessary to carry out a further distillation step in order to separate the n-aldehyde from the iso-aldehyde if the aldehyde product is to be used for production of plasticiser alcohols. It is thus possible to produce an acceptable $C_{10}$-plasticiser alcohol, consisting predominantly of 2-propylheptanol, by submitting the aldehyde product of the process to conventional aldolisation, dehydration and reduction without any need for purification of the intermediate aldehyde.

In order that the invention may be clearly understood and readily carried into effect a preferred hydroformylation process in accordance with the invention will now be described, by way of example only, with reference to the accompanying drawing, which is a diagrammatic flow sheet of a butene hydroformylation plant and of a modification thereof.

Referring to the drawing, a liquid $C_4$-olefin feedstream is passed by line 1 to a pretreatment zone 2 in which it is freed from light sulphurous impurities, such as carbonyl sulphide, hydrogen sulphide, and methyl mercaptan, by passage through consecutive beds of active alumina and zinc oxide and then from chlorinated impurities such as HCl by subsequent passage through a bed of copper-impregnated carbon (Girdler G32J catalyst, obtainable from Girdler Chemicals Inc., of Louisville, Kentucky, United States of America). In passage through the bed of active alumina any COS present is hydrolysed to $H_2S$ due to the presence of traces of water present in the feedstream; the active alumina bed also serves partially to remove $H_2S$ and $CH_3SH$. The zinc oxide bed then removes any remaining $H_2S$ and $CH_3SH$.

The pretreated liquid butenes feedstock passes on via line 3 and then via line 4 to hydroformylation reactor 5.

A 1:1 by volume $H_2$:CO synthesis gas from a partial oxidation plant (not shown) is fed via line 6 to a synthesis gas purification section 7 in which it is treated for removal of metal carbonyls, sulphurous impurities and chlorinated impurities. From purification section 7 the purified synthesis gas is fed via line 8 to reactor 5.

Reactor 5 contains a charge of a liquid reaction medium containing a catalytic amount of a rhodium complex catalyst comprising rhodium complexed with carbon monoxide and triphenylphosphine dissolved in a liquid phase comprising, in addition to product n-valeraldehyde, butenes, and polymeric aldehyde condensation products. It is believed that the major constituents of such polymeric aldehyde condensation products comprise trimers of formulae (C) and (D). The catalytic species is believed to be hydridocarbonyl tris (triphenylphosphine) rhodium (I), which has the formula $HCORh(PPh_3)_3$, and can be generated in situ during the hydroformylation reaction from a suitable catalyst precursor, such as (2,4-pentan-dionato) dicarbonyl rhodium (I), i.e. the rhodium dicarbonyl complex formed with acetylacetone, or rhodium carbonyl triphenylphosphine acetylacetonate. A description of such a hydroformylation catalyst can be found, for example, in U.S. Pat. No. 3,527,809. The use of aldehyde condensation products as a solvent for the rhodium complex catalyst is described in British Patent Specification No. 1338237. In addition to the rhodium complex catalyst the liquid phase in the hydroformylation reactor 5 also contains an excess of triphenylphosphine. The mole ratio of triphenylphosphine to rhodium is approximately 375:1.

The temperature in reactor 5 is maintained at 110° C. by circulating cooling water, or steam, as appropriate, through coil 9.

Liquid reaction medium is continuously removed from reactor 5 via line 10 and passed through a letdown valve 11 and line 12 to a heater 13, which is heated by means of steam passing through line 14. The medium passes on via line 15 to a flash drum 16. A vaporous overhead product passes through demister 17 and exits drum 16 via line 18 to cooler 19. Refrigerant is circulated from refrigeration unit 20 through line 21 to condense butenes and product n-valeraldehyde. From cooler 19 the condensate passes on via line 22 to a product separator 23, from which an overhead gaseous stream is passed to a gas vent through line 24. The condensate is pumped through line 25 by means of pump 26 to a distillation column 27 containing 15 trays. An overhead product comprising mainly mixed butenes is removed overhead from column 27 via line 28 and is condensed in condenser 29, to which cooling water is supplied via line 30. The resulting condensate passes on via line 31 to a reflux drum 32 having a vent line 33.

Liquid condensate is removed from reflux drum 32 via line 34 by means of pump 35. Some of the condensate is returned to column 27 through line 36; the remainder is passed on via line 37. Condensate is recycled to reactor 5 through lines 38 and 4, whilst a liquid purge is taken via line 39.

From flash drum 17 liquid is recycled to reactor 5 through line 40 by means of pump 41.

Reactor 5 is fitted with an overhead take off line 42 which leads to a demister 43. Condensate in demister 43 returns to reactor 5 through line 44. Vapour exiting demister 43 passes through line 45 to a condenser 46, which is fed with cooling water through line 47. Condensate is separated in separator 48 and is returned to reactor 5 through line 49. A gas purge is taken through line 50.

A bottom product, consisting essentially of n-valeraldehyde and containing also a minor proportion of iso-valeraldehyde, is withdrawn from column 27 via line 51. Part of this bottom product is passed to line 52 for purification (e.g. redistillation) and/or further processing and/or storage. The remainder of this bottom product is recycled through line 53, reboiler 54 and line 55 to column 27. Reboiler 54 is heated by means of steam supplied through line 56.

In order to prevent build up of "heavies" in the solution in hydroformylation reactor 5 a bleed stream is removed via line 57 and passed to a regeneration section 58. "Heavies", e.g. valeraldehyde tetramers, believed to be of formulae (F) and (G), and triphenylphosphine oxide are removed by means of line 59. Regenerated solution is recycled to hydroformylation reactor 5 through line 60.

If desired, "heavies" removal zone 58 can be dispensed with. Instead spent reactor solution can be withdrawn from the reactor 5 via line 57 and passed to storage, the rate of withdrawal being sufficient to prevent build up of "heavies" in the reactor 5. At the same time fresh catalyst or catalyst precursor is added via line 60 at a rate sufficient to maintain the rhodium concentration at approximately the chosen level. Such fresh catalyst can be dissolved in an appropriate volume of liquid aldehyde product together with a corresponding amount of free triphenylphosphine. The stored spent catalyst solution can be treated for the recovery of triphenylphosphine and rhodium from which fresh catalyst or catalyst precursor can be manufactured.

A typical method of "heavies" removal in zone 58 involves extraction of the bleed stream in line 57 in a conventional mixer-settler, after cooling to ambient temperature and depressurising, with phosphoric acid or with an aqueous solution of phosphoric acid containing at least about 40% by weight, and preferably at least 60% by weight, of orthophosphoric acid. This phosphoric acid extract, which contains essentially all the active rhodium catalyst and free triphenylphosphine, is then neutralised in the presence of a suitable organic hydrophobic solvent, e.g. n-valeraldehyde trimer, and the resulting organic phase recycled to reactor 5 through line 60 after drying. The organic residue from the phosphoric acid extraction step, on the other hand, is passed to storage via line 59; this organic residue contains catalytically inactive rhodium and triphenylphosphine oxide, as well as high boiling n-valeraldehyde condensation products.

The compositions (in mole %), flow rates, temperatures, and pressures in various of the important lines in the plant are set out below in Table 2. The flow rate in line 35 amounts to 221.15 kg moles/hr, whilst the flow rate in line 36 is 117.30 kg moles/hr.

EXAMPLES

Hydroformylation of a $C_4$-olefin feed gas was effected in a solution containing, in addition to rhodium catalyst and excess triphenylphosphine, product n-valeraldehyde and aldehyde condensation products. The reaction was carried out in a 2000 ml autoclave fitted with a magnetically coupled stirrer and with separate sparge tubes for the $C_4$-olefin feed and for a $CO/H_2$ mixture. Provision was made for off-take of an overhead gaseous product whose pressure could be continuously monitored. The temperature of the autoclave was accurately controlled to within $\pm 0.1°$ C. by means of a combination of electrical heating and air cooling, using an internal air cooling coil. The gas feeds to the autoclave were preheated by passage through tube coils immersed in salt baths. The $CO/H_2$ mixture

TABLE 2

| Component | Line 1 | Line 8 | Line 37 | Line 50 | Line 31 | Line 22 | Line 48 | Line 4 | Line 17 | Line 23 |
|---|---|---|---|---|---|---|---|---|---|---|
| Hydrogen | — | 50.00 | — | — | 19.15 | 22.84 | 22.30 | — | 0.50 | 0.02 |
| Carbon monoxide | — | 48.05 | — | — | 21.28 | 9.80 | 7.41 | — | 0.23 | 0.02 |
| Butene-1 | 69.88 | — | 17.56 | 0.42 | — | 7.67 | 8.57 | 55.21 | 9.69 | 9.73 |
| n-valeraldehyde | — | — | 0.62 | 92.11 | — | 0.31 | 1.19 | 0.17 | 41.43 | 42.32 |
| i-valeraldehyde | — | — | 0.06 | 3.66 | — | — | 0.05 | 0.02 | 1.66 | 1.70 |
| trans-butene-2 | 15.10 | — | 40.53 | 1.48 | — | 13.45 | 17.05 | 22.23 | 22.50 | 22.70 |
| cis-butene-2 | 10.06 | — | 26.81 | 1.22 | — | 7.93 | 10.49 | 14.76 | 14.97 | 15.12 |
| Propane | 0.13 | — | 0.28 | — | — | 0.52 | 0.35 | 0.17 | 0.16 | 0.15 |
| Pentane | 0.54 | — | 0.31 | 0.69 | — | 0.05 | 0.11 | 0.47 | 0.47 | 0.48 |
| n-butane | 2.23 | — | 8.70 | 0.32 | — | 3.02 | 3.70 | 4.05 | 4.83 | 4.87 |
| i-butane | 1.06 | — | 2.63 | 0.04 | — | 1.51 | 1.51 | 1.50 | 1.45 | 1.45 |
| iso-butylene | 1.00 | — | 2.50 | 0.06 | — | 1.15 | 1.27 | 1.42 | 1.38 | 1.38 |
| Nitrogen | — | 1.95 | — | — | 59.57 | 31.75 | 26.00 | — | 0.73 | 0.06 |
| "Heavies" | — | — | — | Trace | — | — | — | — | — | — |
| Flow rate kg moles/hr | 301.07 | 387.76 | 103.85 | 185.53 | 0.43 | 8.70 | 16.78 | 418.37 | 415.81 | 407.11 |
| Temperature °C. | 16 | 177 | 54 | 160 | 55 | −7 | 60 | — | 110 | −7 |
| Pressure kg/cm$^2$ absolute | 12.65 | 12.65 | — | 4.92 | 3.87 | 1.05 | 9.14 | — | 1.55 | 5.98 |

In the plant described above and illustrated in full lines in the drawing liquid reaction medium in line 12 is heated in heater 13 sufficiently to flash off both unreacted butenes and also product n-valeraldehyde. In a modified form of plant a two stage flashing procedure is used. In this form of plant, in which the modifications are shown in broken lines in the drawing, liquid reaction medium in line 12 is heated sufficiently by means of heater 13 to flash off butenes. Instead of passing directly via line 15 to flash drum 16 the medium passes from heater 13 via line 61 to separator 62. Butenes are taken off overhead via line 63 and pass to cooler 64 which is supplied with refrigerant from refrigeration unit 20 by means of line 65. Condensed butenes pass on via line 66 to separator 67 and are recycled to reactor 5 via lines 68, 38 and 4, whilst uncondensed gases are vented via line 69. Liquid from separator 62 passes on via line 70 to a further heater 71 which is supplied with steam via line 72 and thence via line 15 to flash drum 16. In this modified form of plant the size of distillation column 27 can be reduced compared with that of the first-described plant since it has to handle a smaller throughput.

The invention is further illustrated in the following Examples.

was produced by blending the gases upstream from the autoclave and the $CO/H_2$ ratio was adjusted by control of the valves on the gas cylinders.

The autoclave was charged with 300 ml of Filmer 351, the "trimer" of iso-butyraldehyde, with 130 gms triphenylphosphine (TPP), and, as catalyst precursor, with 0.137 gms rhodium in the form of rhodium carbonyl triphenylphosphine acetylacetonate. The autoclave was then heated to 110° C. and the total gas flow (olefins plus synthesis gas) adjusted to 600 liters/hr. In each Example the CO partial pressure was 0.7 kg/cm$^2$ absolute and the $H_2$ partial pressure was 2.8 kg/cm$^2$ absolute. Aldehyde product distilled out of the autoclave and was collected in a water-cooled knock-out pot. The liquid level in the autoclave was maintained constant by pumping back aldehyde product from the knock-out pot. Gas chromatography was used to analyse the product collected in the knock-out pot and to analyse the uncondensed gas, and hence to determine the n-/iso product aldehyde ratio.

The $CO/H_2$ mixture (synthesis gas) was purified by passage through beds of alumina and zinc oxide placed in series and maintained at 180° C. to 200° C. and then over copper-impregnated carbon also maintained at 180° C. to 200° C. The $C_4$-olefin feed was essentially butadiene-free and was purified similarly.

The results are listed below in Table 3.

TABLE 3

| Example No. | Partial pressures kg/cm² abs. | | | n-VAL make gm. moles/ litre/hr | n-/iso- product aldehyde ratio | 3-Me-n-BAL make gm/moles/ litre/hr |
| --- | --- | --- | --- | --- | --- | --- |
| | Butene-1 | Butene-2 | iso-butylene | | | |
| 1 | 0.7 | 0 | 0 | 0.85 | 22/1 | 0 |
| 2 | 0.7 | 1.05 | 0 | 0.85 | 18/1 | 0 |
| 3 | 0.7 | 0 | 1.05 | 0.85 | 22/1 | 0.008 |

Notes:
n-VAL = n-valeraldehyde
3-Me-n-BAL = 3-methyl-n-butyraldehyde, i.e. the product from the hydroformylation of iso-butylene.

We claim:

1. A process for the production of n-valeraldehyde by selective hydroformylation of butene-1 in the presence of at least one other $C_4$-olefin which comprises contacting a $C_4$-olefin feedstock with carbon monoxide and hydrogen in a hydroformylation zone in the presence of a catalytic quantity of a rhodium complex catalyst, said $C_4$-olefin feedstock comprising butene-1 and at least one other $C_4$-olefin selected from cis-butene-2, trans-butene-2, and iso-butylene and said rhodium complex catalyst comprising rhodium in complex combination with carbon monoxide and a triorganophosphine ligand, and in the presence of at least about 100 moles of free triorganophosphine ligand per gram atom of rhodium, at a temperature in the range of from about 80° C. to about 130° C., and at a total pressure of not more than about 50 kg/cm² absolute, the partial pressure of carbon monoxide being less than about 1.5 kg/cm² absolute and the partial pressure of hydrogen being in the range of from about 1.0 to about 7.5 kg/cm² absolute, and recovering from the hydroformylation zone unreacted $C_4$-olefins and n-valeraldehyde, said unreacted $C_4$-olefins including substantially all of said at least one other $C_4$-olefin present in the feedstock.

2. A process according to claim 1, in which the temperature in the hydroformylation zone ranges from about 90° C. to about 110° C.

3. A process according to claim 1 or claim 2, in which the total pressure is in the range of from about 4 to about 20 kg/cm² absolute.

4. A process according to claim 3, in which the partial pressure of carbon monoxide ranges from about 0.5 to about 1.0 kg/cm² absolute.

5. A process according to claim 3, in which the partial pressure of hydrogen ranges from about 1.25 to about 3.0 kg/cm² absolute.

6. A process according to claim 3 in which the partial pressure of butene-1 ranges from about 0.4 to about 1.5 kg/cm² absolute.

7. A process according to claim 1 or 2, in which the feedstock comprises from about 20 mole % up to about 80 mole % of butene-1.

8. A process according to claim 1 or 2, in which the triorganophosphine is triphenylphosphine.

9. A process for the production of n-valeraldehyde by selective hydroformylation of butene-1 in the presence of at least one other $C_4$-olefin which comprises:
(i) providing a hydroformylation zone containing a liquid charge comprising (a) a rhodium complex catalyst wherein rhodium is in complex combination with carbon monoxide and a triorganophosphine, (b) excess free triorganophosphine in an amount of at least about 100 moles per gram atom of rhodium, (c) liquid n-valeraldehyde product, and (d) polymeric aldehyde condensation products;
(ii) feeding a liquid $C_4$-olefin feedstock to the hydroformylation zone, said $C_4$-olefin feedstock comprising butene-1 and at least one other $C_4$-olefin selected from cis-butene-2, trans-butene-2, and iso-butylene;
(iii) supplying make up hydrogen and carbon monoxide to the hydroformylation zone;
(iv) maintaining in the hydroformylation zone a temperature in the range of from about 80° C. to about 130° C., a total pressure of not more than about 50 kg/cm² absolute, a partial pressure of butene-1 of less than about 4.0 kg/cm² absolute, a partial pressure of carbon monoxide of less than about 1.5 kg/cm² absolute and a partial pressure of hydrogen of from about 1.0 to about 7.5 kg/cm² absolute;
(v) recovering from the hydroformylation zone a liquid reaction product;
(vi) reducing the pressure of the liquid reaction product;
(vii) thereafter flashing unreacted $C_4$-olefins and product n-valeraldehyde from the liquid reaction product, said unreacted $C_4$-olefins including substantially all of said at least one other $C_4$-olefin present in the feedstock;
(viii) recycling resulting liquid reaction residue, now depleted in the $C_4$-olefins and product n-valeraldehyde, to the hydroformylation zone;
(ix) condensing product n-valeraldehyde and unreacted $C_4$-olefins; and
(x) recycling unreacted $C_4$-olefins to the hydroformylation zone.

10. A process according to claim 9, in which pressure reduction in step (vi) is effected at or below reaction temperature.

11. A process according to claim 3, wherein the feedstock comprises from about 20 mole % up to about 80 mole % of butene-1.

12. A process according to claim 11, wherein the triorganophosphine is triphenylphosphine.

13. A process according to claim 11, wherein:
(a) the partial pressure of carbon monoxide ranges from about 0.5 to about 1.0 kg/cm² absolute;
(b) the partial pressure of hydrogen ranges from about 1.25 to about 3.0 kg/cm² absolute; and
(c) the partial pressure of butene-1 ranges from about 0.4 to about 1.5 kg/cm² absolute.

14. A process according to claim 13 wherein the triorganophosphine is triphenylphosphine.

* * * * *